(12) United States Patent
Liu et al.

(10) Patent No.: US 10,336,835 B2
(45) Date of Patent: Jul. 2, 2019

(54) POLYMORPHS OF SUGAMMADEX AND PROCESS FOR PREPARATION OF SUGAMMADEX

(71) Applicant: FORMOSA LABORATORIES, INC., Taoyuan (TW)

(72) Inventors: Yu-Liang Liu, Taoyuan (TW); Ching-Peng Wei, Taoyuan (TW)

(73) Assignee: FORMOSA LABORATORIES, INC., Taoyuan (TW)

( * ) Notice: Subject to any disclaimer, the term of this patent is extended or adjusted under 35 U.S.C. 154(b) by 136 days.

(21) Appl. No.: 15/683,797

(22) Filed: Aug. 23, 2017

(65) Prior Publication Data
US 2019/0062460 A1    Feb. 28, 2019

(51) Int. Cl.
*C08B 37/00* (2006.01)
*C08B 37/16* (2006.01)
*A61K 31/724* (2006.01)

(52) U.S. Cl.
CPC ........ *C08B 37/0012* (2013.01); *A61K 31/724* (2013.01); *C08B 37/00* (2013.01)

(58) Field of Classification Search
None
See application file for complete search history.

(56) References Cited

FOREIGN PATENT DOCUMENTS

WO    WO-2017163165 A1 *  9/2017  ......... C08B 37/0012

* cited by examiner

*Primary Examiner* — Traviss C McIntosh, III
(74) *Attorney, Agent, or Firm* — Hannah Tien

(57) ABSTRACT

The present invention provides a crystalline form of Suagmmadex sodium, characterized by an X-ray powder diffraction pattern. The present invention further provides crystalline forms of Suagmmadex sodium for use in the manufacture of a pharmaceutical composition or a medicament. The present invention further provides a pharmaceutical composition comprising the crystalline form of Sugammadex sodium of the present invention and at least one pharmaceutical acceptable excipient.

10 Claims, 3 Drawing Sheets

POLYMORPHS OF SUGAMMADEX AND PROCESS FOR PREPARATION OF SUGAMMADEX

FIELD OF THE INVENTION

The present invention relates to novel crystalline forms of Sugammadex sodium, which can be characterized by an X-ray powder diffraction pattern.

BACKGROUND OF THE INVENTION

Sugammadex is first disclosed in U.S. Pat. No. 6,670,340 assigned to Akzo Nobel. Sugammadex sodium was approved in European Medicines Agency as an agent for reversal of neuromuscular blockade by the agent rocuronium in general anaesthesia in 2008 and is the first selective relaxant binding agent (SRBA).

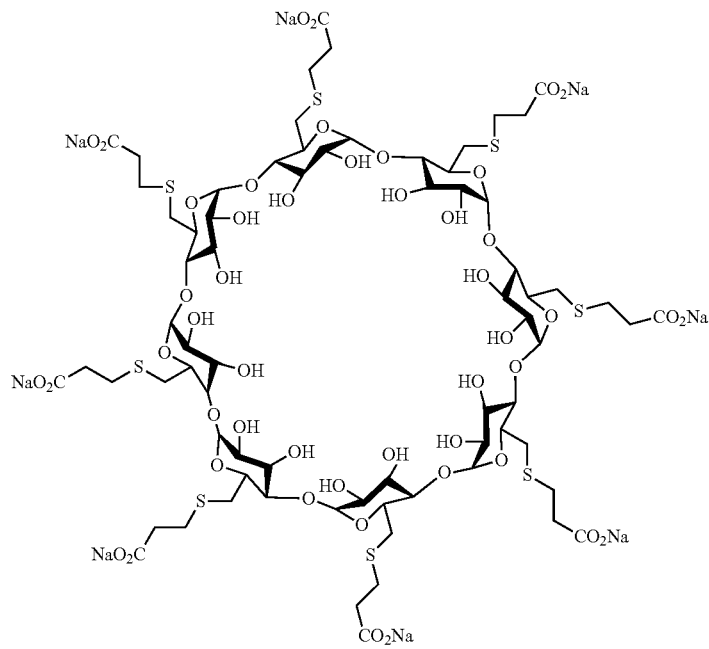

Sugammadex sodium contains 8 recurring glucose units each with 5 asymmetric carbon atoms, in total 40 asymmetric carbon atoms for the whole molecule. Sugammadex is a modified γ-cyclodextrin, with a lipophilic core and a hydrophilic periphery. The gamma cyclodextrin has been modified from its natural state by placing eight carboxyl thio ether groups at the sixth carbon positions.

Polymorphism, the occurrence of different crystal forms, is a property of some molecules and molecular complexes. A single molecule, like Sugammadex, may give rise to a variety of polymorphs having distinct crystal structures and physical properties like melting point, thermal behaviors (e.g. measured by thermogravimetric analysis, or differential scanning calorimetry), X-ray diffraction pattern, infrared absorption fingerprint, and solid state NMR spectrum. One or more of these techniques may be used to distinguish different polymorphic forms of a compound.

Discovering new polymorphic forms and solvates of a pharmaceutical product can provide materials having desirable processing properties, such as ease of handling, ease of processing, storage stability, and ease of purification or as desirable intermediate crystal forms that facilitate conversion to other polymorphic forms. New polymorphic forms and solvates of a pharmaceutically useful compound or salts thereof can also provide an opportunity to improve the performance characteristics of a pharmaceutical product. It enlarges the repertoire of materials that a formulation scientist has available for formulation optimization, for example by providing a product with different properties, e.g., better processing or handling characteristics, improved dissolution profile, or improved shelf-life. For at least these reasons, there is a need for additional polymorphs of Sugammadex sodium.

SUMMARY OF THE INVENTION

The present invention provides a novel crystalline form of Sugammadex sodium, wherein the crystalline form of Sugammadex sodium is a polymorph of Form I, Form II or Form III.

DETAILED DESCRIPTION OF THE INVENTION

The present invention provides a novel crystalline form of Sugammadex sodium, wherein the crystalline form of Sugammadex sodium is a polymorph of Form I, Form II or Form III.

As recited herein, all numbers should be considered modified by the term "about".

As used herein, "a," "an," "the," "at least one," and "one or more" are used interchangeably.

In general, polymorphism refers to the ability of a substance to exist as two or more crystalline forms that have different spatial arrangements and/or conformations of molecules in their crystal lattices. Thus, polymorphs refer to different crystalline forms of the same pure substance in which the molecules have different spatial arrangements of the molecules, atoms, and/or ions forming the crystal. Different polymorphs may have different physical properties Such as melting points, solubilities, X-ray diffraction patterns, etc.

Polymorphism may also include solvation or hydration products (also known as pseudopolymorphs) and amorphous forms. Differences in these forms could, in some cases, affect the quality or performance of the new drug products.

The crystalline forms of Sugammadex sodium described herein have advantageous properties selected from at least one of: chemical purity, flowability, solubility, morphology or crystal habit, stability—such as storage stability, stability to dehydration, stability to polymorphic conversion, low hygroscopicity, and low content of residual solvents.

Figure 1:
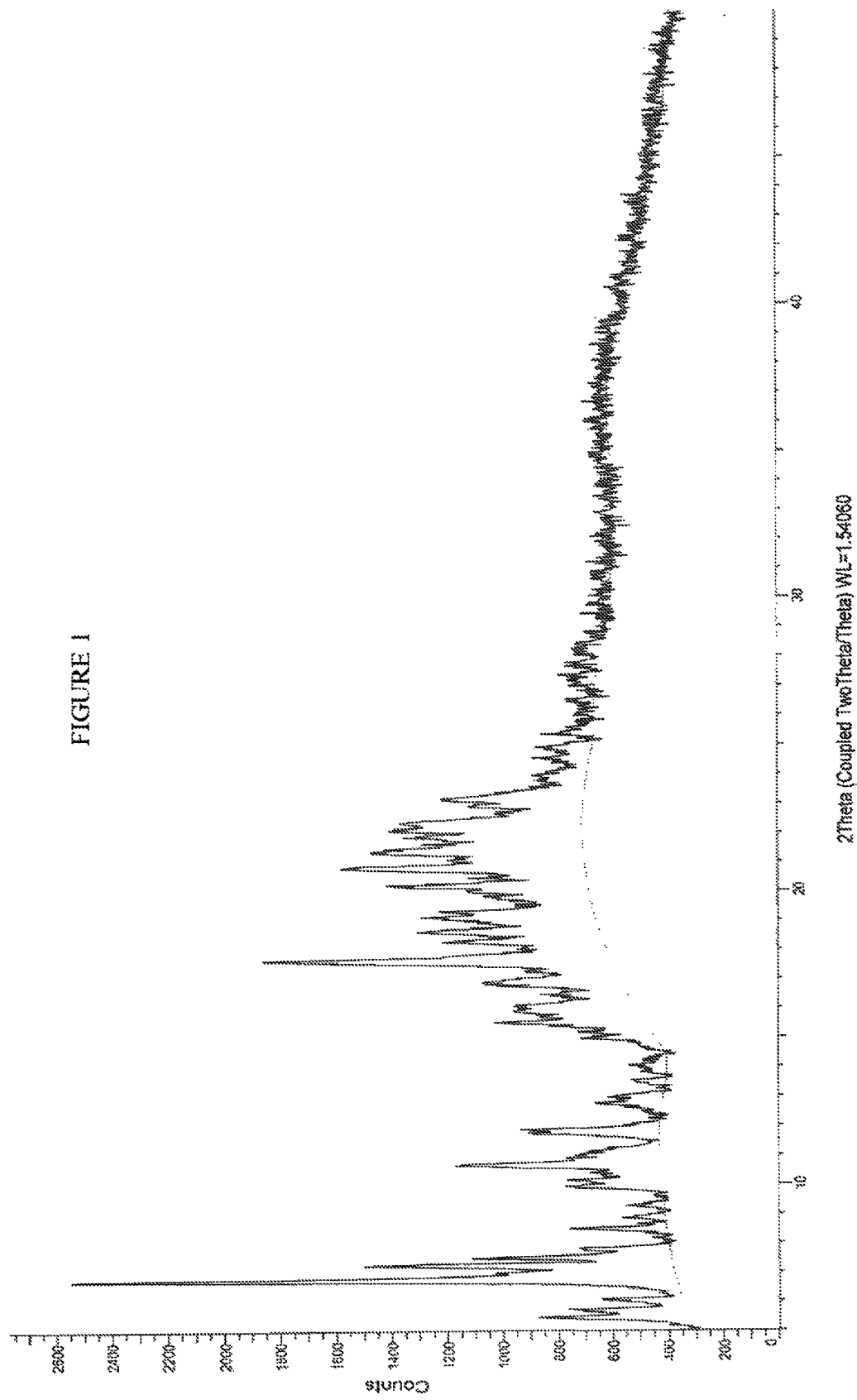
FIG. 1 is an illustration of a XRPD pattern of crystalline Form I of Sugammadex sodium.

In one embodiment, the present invention provides a crystalline form of Sugammadex sodium, designated herein as Form I. Form I can be characterized by an X-ray powder diffraction pattern having peaks at 6.7, 7.2, 17.6, 20.8 and 21.4 degrees 2-theta±0.2 degrees 2-theta; an X-ray powder diffraction pattern substantially as depicted in FIG. 1; and combination thereof. Preferably, the crystalline form can be further characterized by an X-ray powder diffraction pattern having one, two, three, four or five peaks selected from 7.5, 10.7, 20.2, 22.2, and 22.3 degrees 2-theta±0.2 degrees 2-theta. More preferably, it includes five or more peaks at angles of refraction 2-theta: selected from the group consisting of 5.5, 5.6, 6.0, 6.7, 7.2, 7.5, 7.7, 8.5, 8.9, 9.3, 10.0, 10.1, 10.7, 11.8, 12.8, 12.9, 13.5, 13.9, 14.2, 14.7, 15.0, 15.5, 16.0, 16.5, 16.9, 17.6, 18.3, 18.6, 19.1, 19.3, 19.8, 20.2, 20.8, 21.4, 21.9, 22.2, 22.3, 23.0, 23.2, 23.9, 24.5, 24.9, 25.4, 26.5, and 40.5±0.2 degrees 2-theta.

Figure 2:
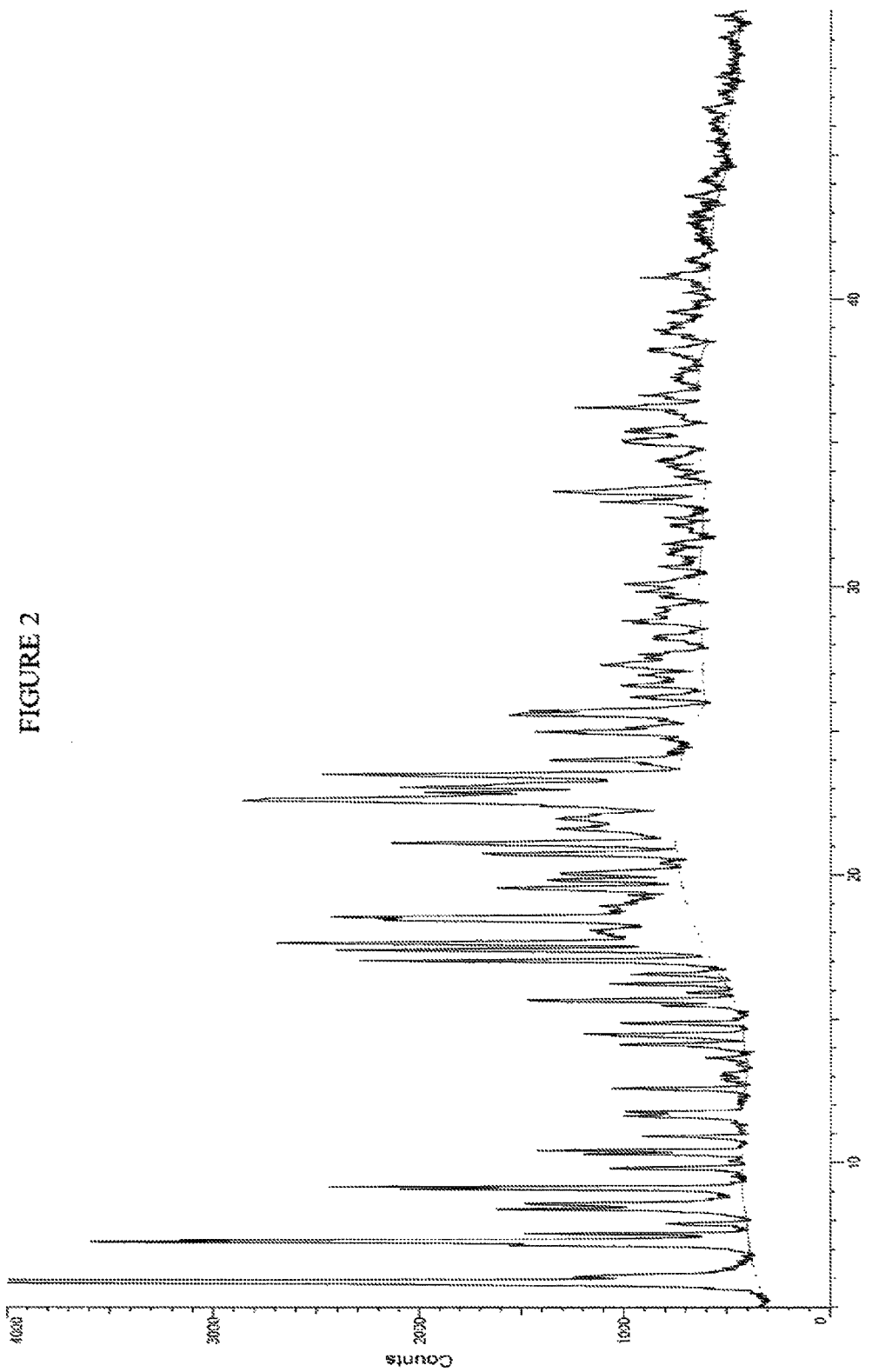
FIG. 2 is an illustration of a XRPD pattern of crystalline Form II of Sugammadex sodium.

In one embodiment, the present invention provides a crystalline form of Sugammadex sodium, designated herein as Form II. Form II can be characterized by an X-ray powder diffraction pattern having peaks at 5.9, 7.27, 7.31, 17.6 and 22.6 degrees 2-theta±0.2 degrees 2-theta; an X-ray powder diffraction pattern substantially as depicted in FIG. 2; and combination thereof. Preferably, the crystalline form can be further characterized by an X-ray powder diffraction pattern having one, two, three, four or five peaks selected from 9.2, 17.0, 17.4, 18.6, and 22.65 degrees 2-theta±0.2 degrees 2-theta. More preferably, it includes five or more peaks at angles of refraction 2-theta: selected from the group consisting of 5.9, 6.1, 7.2, 7.3, 7.3, 7.6, 7.9, 8.4, 8.6, 9.1, 9.2, 9.8, 10.3, 10.4, 10.9, 11.6, 11.8, 12.6, 13.0, 14.1, 14.5, 14.9, 15.5, 15.7, 15.9, 16.2, 16.6, 17.0, 17.4, 17.6, 18.5, 18.6, 19.6, 19.8, 20.1, 20.7, 21.1, 21.1, 21.6, 22.6, 22.6, 22.9, 23.1, 23.5, 24.0, 25.0, 25.0, 25.6, 25.7, 26.1, 26.6, 26.6, 28.8, 28.8, 29.7, 30.1, 30.7, 32.4, 33.0, 33.3, 33.3, 35.4, 36.2, 39.5, 40.8 and 47.7±0.2 degrees 2-theta.

Figure 3:
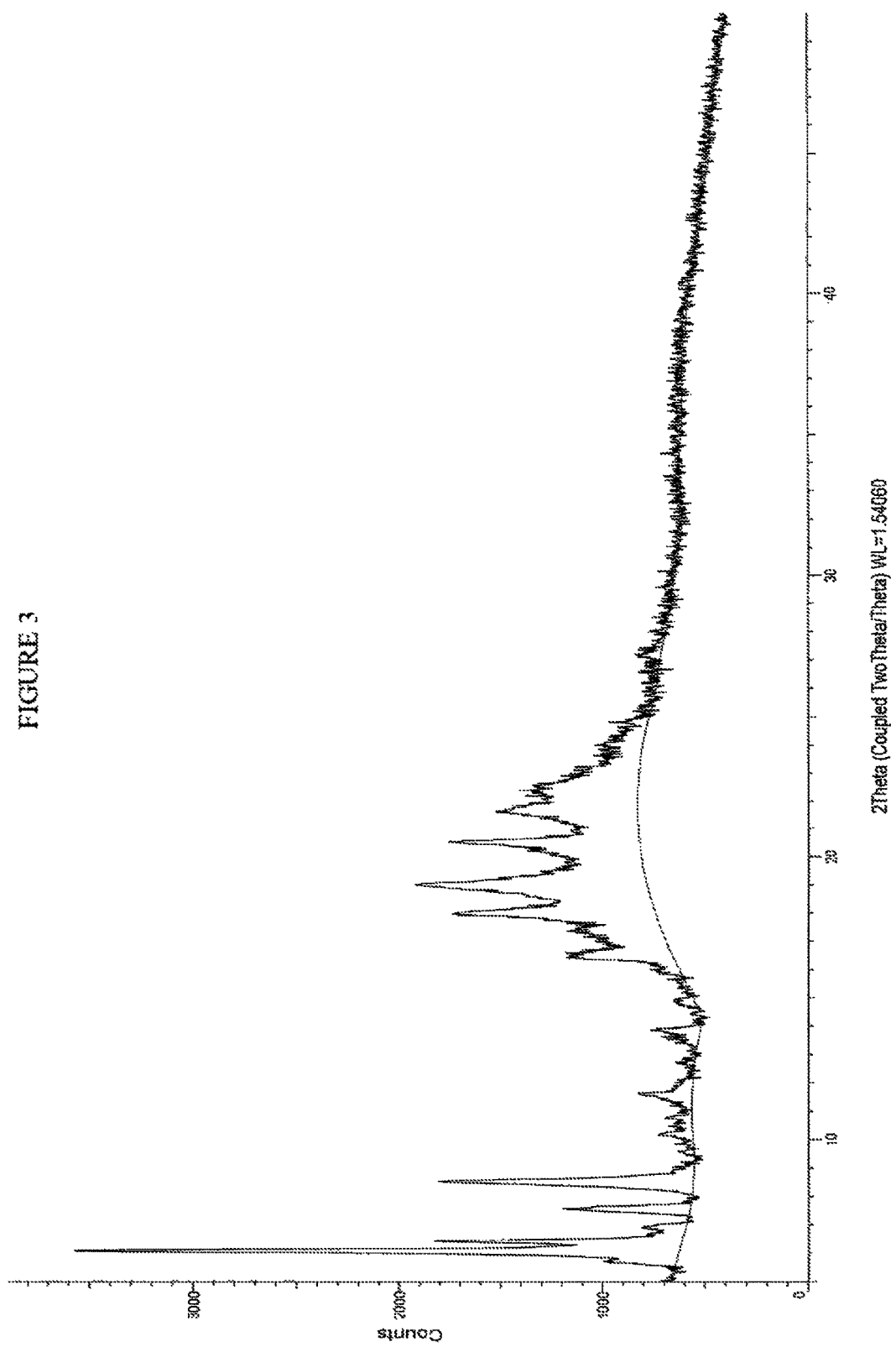
FIG. 3 is an illustration of a XRPD pattern of crystalline Form III of Sugammadex sodium.

In one embodiment, the present invention provides a crystalline form of Sugammadex sodium, designated herein as Form III. Form III can be characterized by data selected from: an X-ray powder diffraction pattern having peaks at 6.1, 6.4, 8.5, 18.0 and 19.0 degrees 2-theta±0.2 degrees 2-theta; an X-ray powder diffraction pattern having peaks at 6.1, 8.5, 18.0, 19.0, and 20.5 degrees 2-theta±0.2 degrees 2-theta; and combinations thereof; an X-ray powder diffraction pattern substantially as depicted in FIG. 3; and combination thereof. Form III can be alternatively characterized by an X-ray powder diffraction pattern having peaks at 6.1, 6.4, 8.5, 18.0 and 19.0 degrees 2-theta±0.2 degrees 2-theta and also having an additional one, two, three, four or five peaks selected from 7.6, 16.5, 17.4, 20.5, and 21.6 degrees 2-theta±0.2 degrees 2-theta. In another embodiment, it includes five or more peaks at angles of refraction 2-theta: selected from the group consisting of 5.8, 6.1, 6.4, 6.9, 7.8, 8.5, 10.2, 10.7, 11.6, 13.6, 13.7, 13.8, 14.9, 16.0, 16.5, 17.4, 18.0, 19.0, 20.5, 21.6, 24.8, and 27.2±0.2 degrees 2-theta.

In another embodiment, Form III can be alternatively characterized by an X-ray powder diffraction pattern having peaks at 6.1, 8.5, 18.0, 19.0, and 20.5 degrees 2-theta±0.2 degrees 2-theta and also having an additional one, two, three, four or five peaks selected from 6.4, 16.5, 20.2, 21.6, and 22.4 degrees 2-theta±0.2 degrees 2-theta. In yet another embodiment, it includes five or more peaks at angles of refraction 2-theta: selected from the group consisting of 5.8, 6.1, 6.4, 6.9, 7.6, 8.5, 10.2, 10.8, 11.6, 12.0, 12.7, 13.6, 13.8, 14.8, 15.5, 16.0, 16.5, 17.4, 18.0, 19.0, 20.2, 20.5, 21.6, 22.4, and 23.1±0.2 degrees 2-theta.

In one embodiment, the present invention further provides a use of any one or combination of the above described crystalline forms in the manufacture of a pharmaceutical composition or a medicament.

In one embodiment, the present invention further provides a pharmaceutical composition comprising one or more of the above described crystalline forms and at least one pharmaceutically acceptable excipient.

EXAMPLE

To demonstrate the benefits of the present invention, examples of the prior art were reworked and indicated as reference example.

Reference Example 1 (Example 4 of WO2001/040316 A1)

Preparation of 6-Per-deoxy-6-per-(2-carboxyethyl) thio-γ-cyclodextrin, Sodium Salt 3-Mercaptopropionic acid (1.22 ml, 14.0 mmol) was dissolved in dry DMF (45 ml) under $N_2$ at room temperature. To this solution was added in three portions sodium hydride (1.23 g, 30.8 mmol, 60%) and the mixture was stirred for a further 30 min. To the mixture was then added dropwise a solution of 6-per-deoxy-6-per-iodo-γ-cyclodextrin (3.12 g, 1.40 mmol) in 45 ml thy DMF. After addition, the reaction mixture was heated at 70° C. for 12 h. After cooling, water (10 ml) was added to the mixture and the volume was reduced to 40 ml in vacuo, to which ethanol (250 ml) was added resulting in precipitation. The solid precipitation was collected by filtration and dialysed for 36 h. The volume was then reduced to 20 ml in vacuo. To this was added ethanol, and the precipitate was collected by filtration and dried to give the title compound as a white solid (1.3 g, 43%).

Reference Example 2

Sugammadex sodium white solid (1.3 g) was dissolved in water (5 ml). To the aqueous solution was added dropwisely in dry DMF (8.5 ml), the solution turned turbid, then was added in more dry DMF (14 ml) to form precipitate. The resulting solution was concentrated and volume was reduced to 20 ml in vacuo. The absolute ethanol was added resulting in crystallization. The crystalline powder was collected by filtration and dried to give the title compound (1.04 g, 80%).

Reference Example 3

Sugammadex sodium white solid (1.3 g) was dissolved in water (5 ml). To the aqueous solution was added dropwisely in dry DMF (8.5 ml), the solution turned turbid, then was added in more dry DMF (14 ml) to form precipitate. The resulting solution was concentrated and volume was reduced to 20 ml in vacuo. The 95% ethanol was added resulting in crystallization. The crystalline powder was collected by filtration and dried to give the title compound (1.11 g, 85%).

Example 1: Preparation of 6-per-deoxy-6-per-bromo-γ-cyclodextrin

To a reaction flask, DMF (1.7 Kg), Tributylphosphine ($Bu_3P$) (540 g, 2.67 mol) were added and stir about 5 min. Bromine (420 g, 2.63 mol) was added to the reaction flask, kept the temperature at 20° C.–30° C. and stir for 20 min, Gamma-cyclodextrin (180 g, 0.139 mol) was suspended in DMF (850 g), and added to the reaction flask. After the addition, reaction mixture was heated to about 70° C. and stir for 4-6 hrs. 25% Sodium methoxide solution (580 g) and MeOH (480 g) was added to quench the reaction, concentrated to remove methanol, and then water (4.5 Kg) was added to form the precipitate. The crude Suga-1 was washed with water (200 g).

To a reaction flask, isopropanol (IPA) (2.83 Kg), crude Suga-1 were added. The reaction mixture was heated to 35° C.~50° C., stir for 1 hr to remove tributylphosphine oxide (TBPO), then recrystallization from DMF (380 g)/IPA2.83 Kg) solvent. The title compound (170 g) was obtained after filtration and washed with IPA (500 g).

Example 2: Preparation of 6-per-(2-carboxyethyl)thio-γ-cyclodextrin, methyl ester To a reaction flask, DMF (400 g), 60% NaH (50 g) were added under $N_2$. After the addition, the reaction mixture was de-gased and purged with $N_2$ literally three times. Methyl 3-mercaptopropionate (210 g, 1.75 mol), DMF (400 g) were added to the reaction flask which were cooled to −10° C.~0° C. during the period of addition. After the addition, the temperature of the reaction flask was risen to −5° C.~0° C. Suga-1 (170 g, 0.97 mol) in DMF (810 g) solution was added to the reaction mixture and stir for 1-1.5 hrs. The reaction was completed by check with HPLC. Water (2.88 Kg), ammonium chloride (320 g) aqueous solution were added to quench the reaction. The precipitate was formed gradually. The mixture was filtered, and the crude Suga-2 was obtained after washed with water (400 g). The pure title compound (200 g) white powder was obtained by recrystallization from Acetonitrile (1.57 Kg)/water (1 Kg) solution.

Example 3: Preparation of 6-per-(2-carboxyethyl)thio-γ-cyclodextrin, Sodium Salt To a reaction flask, 1N NaOH (30 g), water (700 g) aqueous solution, Suga-2 was added under $N_2$. The reaction mixture was stirred for 16~17 hrs. The pH of clear reaction solution was adjusted to 9~10 with 32% hydrochloride (10 g), water (140 g) aqueous solution, then methanol (1.5 Kg) was added to form white powder of crude Suga-Na. Pure wet Suga-Na was obtained by recrystallization from methanol (330 g)/water (140 g) solution.

Example 4: Purification and Isolation of Crystalline Form I of 6-per-(2-carboxyethyl)thio-γ-cyclodextrin, Sodium Salt (Suagmmadex Sodium)

To a solution of 6-per-(2-carboxyethyl)thio-γ-cyclodextrin, sodium salt (1 g) in water (3 ml) was added DMF (7.5 ml) resulting in crystallization. The suspension was stirred for 1 h at 25° C., filtered and the cake was washed two time with a mixture of water and DMF to obtain crystalline form I of 6-per-(2-carboxyethyl)thio-γ-cyclodextrin, sodium salt. HPLC purity: 98.2%.

Example 5: Purification and Isolation of Crystalline Form II of 6-per-(2-carboxyethyl)thio-γ-cyclodextrin, Sodium Salt (Suagmmadex Sodium)

To a solution of 6-per-(2-carboxyethyl)thio-γ-cyclodextrin, sodium salt (93 g) in water (3 ml) was added MeOH (480 ml) resulting in crystallization. The suspension mixture was heated to 65° C., the solution turned clear. The mixture was cooled slowly. The crystals formed after the temperature lowered to about 42~45° C. and stirred for 2 hr. The suspension was stirred for 2 h at 25° C., filtered and the cake was washed two time with a mixture of water and MeOH to obtain crystalline form II of 6-per-(2-carboxyethyl)thio-γ-cyclodextrin, sodium salt (75 g, yield 80.6%). HPLC purity: 99.3%.

Example 6: Isolation of Crystalline Form III of 6-per-(2-carboxyethyl)thio-γ-cyclodextrin, Sodium Salt (Suagmmadex Sodium)

The crystalline form II of 6-per-(2-carboxyethyl)thio-γ-cyclodextrin, sodium salt (0.5 g) from example 5 was dried in vacuo (15 mmHg), at 80° C. for 12 h to obtain crystalline form III of 6-per-(2-carboxyethyl)thio-γ-cyclodextrin, sodium salt.

Example 7: Isolation of Crystalline form III of 6-per-(2-carboxyethyl)thio-γ-cyclodextrin, Sodium Salt (Suagmmadex Sodium)

The crystalline form II of 6-per-(2-carboxyethyl)thio-γ-cyclodextrin, sodium salt (0.5 g) from example 5 was dried in vacuo (15 mmHg), at 90° C. for 12 h to obtain crystalline form III of 6-per-(2-carboxyethyl)thio-γ-cyclodextrin, sodium salt.

Example 8: Isolation of Amorphous Form of 6-per-(2-carboxyethyl)thio-γ-cyclodextrin, Sodium Salt (Suagmmadex Sodium)

The wet Sugammadex sodium powder was dissolved in water (2 Kg). The solution (5% Sugammadex sodium aqueous solution) was filtered with 0.2 μm filter paper prior to be performed the drying procedure. The amorphous form of Sugammadex sodium was obtained by Spray-dryer.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. A crystalline form of Suagmmadex sodium, characterized by an X-ray powder diffraction pattern having peaks at 6.7, 17.6, 7.2, 20.8 and 21.4 degrees 2-theta±0.2 degrees 2-theta.

2. The crystalline form of claim 1, further characterized by an X-ray powder diffraction pattern having one, two, three, four or five peaks selected from 7.5, 10.7, 20.2, 22.2, 22.3 degrees 2-theta±0.2 degrees 2-theta.

3. A crystalline form of Suagmmadex sodium, characterized by an X-ray powder diffraction pattern having peaks at 5.9, 7.27, 7.31, 17.6 and 22.6 degrees 2-theta±0.2 degrees 2-theta.

4. The crystalline form of claim 3, further characterized by an X-ray powder diffraction pattern having one, two, three, four or five peaks selected from 9.2, 17.0, 17.4, 18.6, and 22.65 degrees 2-theta±0.2 degrees 2-theta.

5. A crystalline form of Suagmmadex sodium, characterized by data selected from: an X-ray powder diffraction pattern having peaks at 6.1, 6.4, 8.5, 18.0 and 19.0 degrees 2-theta±0.2 degrees 2-theta; an X-ray powder diffraction pattern having peaks at 6.1, 8.5, 18.0, 19.0, and 20.5 degrees 2-theta±0.2 degrees 2-theta.

6. The crystalline form of claim 5, characterized by an X-ray powder diffraction pattern having peaks at 6.1, 6.4, 8.5, 18.0 and 19.0 degrees 2-theta±0.2 degrees 2-theta.

7. The crystalline form of claim 6, further characterized by an X-ray powder diffraction pattern having one, two, three, four or five peaks selected from 7.6, 16.5, 17.4, 20.5, and 21.6 degrees 2-theta±0.2 degrees 2-theta.

8. The crystalline form of claim 5, characterized by an X-ray powder diffraction pattern having peaks at 6.1, 8.5, 18.0, 19.0, and 20.5 degrees 2-theta±0.2 degrees 2-theta.

9. The crystalline form of claim 8, further characterized by an X-ray powder diffraction pattern having one, two, three, four or five peaks selected from 6.4, 16.5, 20.2, 21.6, and 22.4 degrees 2-theta±0.2 degrees 2-theta.

10. A pharmaceutical composition comprising the crystalline form of Sugammadex sodium according to any one of claims 1 to 9 and at least one pharmaceutical acceptable excipient.

* * * * *